United States Patent [19]

Temeyer et al.

[11] Patent Number: 4,945,057

[45] Date of Patent: Jul. 31, 1990

[54] **MONOCLONAL ANTIBODIES TO CRYSTAL PROTEIN OF *BACILLUS THURINGIENSIS* SUBSPECIES *ISRAELENSIS***

[75] Inventors: Kevin B. Temeyer, San Antonio; Maurice Haufler; John H. Pruett, both of Kerrville, all of Tex.

[73] Assignee: The United States of America as represented by the Secretary of Agriculture, Washington, D.C.

[21] Appl. No.: 50,451

[22] Filed: May 18, 1987

[51] Int. Cl.$^5$ .................. C12N 5/20; C07K 15/28
[52] U.S. Cl. .................. 435/240.27; 435/70.21; 435/172.2; 435/948; 435/832; 530/387; 530/809; 530/825; 436/548; 935/104; 935/108; 935/110; 935/93
[58] Field of Search .................. 435/240.27, 172.2, 68, 435/832, 70.21, 948; 530/387, 388, 809, 350, 825; 935/90, 92, 93, 104, 108, 110

[56] References Cited

PUBLICATIONS

Hurley, J. M. et al., "Separation of the Cytolytic and Mosquitocidal Proteins of *Bacillus thuringiensis* subsp. *israeleusis*", *Biochem. Biophys. Res. Commun.*, 126(2): 961–965, Jan. 31, 1985.

Lee, S. G. et al., "Diversity of Protein Inclusion Bodies and Identification of Mosquitocidal Protein in *Bacillus thuringiensis* subsp. *israelensis*", *Biochem. Biophys. Res. Commun.*, 126(2): 953–960, Jan. 31, 1985.

Armstrong, J. L. et al., "Delta Endotoxin of *Bacillus thuringiensis* subsp. *israelensis*", *J. Bacteriol.*, 161(1): 39–46, Jan. 1985.

Temeyer, K. B. et al., "Production and Use of Monoclonal Antibodies Specific for Crystal Protein of *Bacillus thuringiensis* var. *israelensis*", *J. Cell. Biochem.*, Suppl. 10C:92, Mar. 30–Apr. 12, 1986.

Huber-Lukac, M. et al., Experientia, 38, pp. 1103–1105, (1982).

Huber-Lukac, M. et al., American Society for Microbiology, 40:2, pp. 608–612, (May 1983).

Huber-Lukac, M. et al., Infection and Immunity, 54:1, pp. 228–232, (1986).

Temeyer, Kevin B., Applied and Environmental Microbiology, 47:5, pp. 952–955, (May 1984).

Zola, H. and D. Brooks, "Techniques for the Production and Characterization of Monoclonal Hybirdoma Antibodies", *Monoclonal Hybridoma AntiBodies: Techniques and Applications*, pp. 1–57.

*Primary Examiner*—Margaret Moskowitz
*Assistant Examiner*—Kay E. Cheney
*Attorney, Agent, or Firm*—M. Howard Silverstein; Curtis P. Ribando; David Sadowski

[57] ABSTRACT

Murine hybridomas are disclosed which were constructed by fusing spleen cells from BALB/c mice immunized with soluble crystal protein from *Bacillus thuringiensis* subsp. *israelensis* (B.t.i.) to the murine myeloma cell line SP2/0-AG14. An ELISA (enzyme-linked immunosorbent assay) method for detection of antibodies specific for crystal protein of B.t.i. was modified to produce 100- to 1,000-fold increased sensitivity and was used to identify hybridomas secreting monoclonal antibody specific for the B.t.i. crystal protein. Analysis of the hybridoma culture supernatant fluid indicated production of monoclonal IgG3 antibodies, specific for the 68,000 dalton protein presumed to be the insecticidal delta-endotoxin of B.t.i.

2 Claims, No Drawings

MONOCLONAL ANTIBODIES TO CRYSTAL PROTEIN OF *BACILLUS THURINGIENSIS* SUBSPECIES *ISRAELENSIS*

BACKGROUND OF THE INVENTION (1) Field of the Invention

This invention relates to immunochemicals for use with microbial pesticides. More particularly this invention is for monoclonal antibodies to crystal proteins of *Bacillus thuringiensis* subsp. *israelensis* and to the hybrid cell lines that secrete these monospecific antibodies.

(2) Description of the Prior Art

*Bacillus thuringiensis* is an aerobic, endospore-forming, Gram positive bacterium which forms a proteinaceous crystalline inclusion during sporulation and is pathogenic to certain insects. Monoclonal antibodies to *Bacillus thuringiensis* have been reported for crystal protein only of subsp. *thuringiensis* and *kurstaki* (Huber-Lukac et al., 1982, 1983, 1986). The crystal protein of *B. thuringiensis* subsp. *israelensis* is larvicidal to several families of Dipteran insects, including mosquitoes, black flies, midges, and horn flies (Temeyer 1984). Crystals prepared from *B. thuringiensis* subsp. *israelensis* contain several proteins and there is some controversy over which of these component proteins represents the insecticidal toxin (delta-endotoxin) active in vivo. Molecular biological techniques are capable of resolving this controversy, but are complicated by potential proteolysis of crystal protein components during preparation as well as difficulty in assaying insecticidal activity of soluble proteins.

One method of production of monoclonal antibodies by the fusion of spleen cells from immunized mice and myeloma cells grown in continuous culture has been described previously by Zola & Brooks (1982). However, it should be noted that preparation of hybridoma cell populations remains unpredictable, and one cannot extrapolate from one antigen or cell system to another.

Heretofore, monoclonal antibodies specific for different component proteins of *B. thuringiensis* subsp. *israelensis* crystals were not available.

SUMMARY OF THE INVENTION

We have prepared a hybrid cell line which secretes monoclonal antibody specific for a protein component of the insecticidal crystalline inclusion of *Bacillus thuringiensis* subsp. *israelensis*. The novel antibody produced by the hybridoma of our invention is specific for crystal protein of *B. thuringiensis* subsp. *israelensis* and does not cross-react with crystal proteins of *B. thuringiensis* subspecies specifically toxic to lepidopteran insects. Because of this novel specificity, our invention allows specific immunochemical techniques to be utilized for biochemical and immunochemical study, immunoaffinity preparation, or genetic manipulation of crystal proteins derived from *B. thuringiensis* subsp. *israelensis* through use of recombinant DNA technology and immunochemical screening.

In addition, because the monoclonal antibody of the invention is specific for a protein derived from *B. thuringiensis* subsp. *israelensis*, it provides a means of monitoring use and distribution of *B. thuringiensis* subsp. *israelensis* in the environment, as well as the ability to monitor novel organisms resulting from recombinant DNA technology which contain and express the specific structural genes which specify the protein or derivative proteins recognized by the antibody. Accordingly, immunochemical methods for using the monoclonal antibody have been developed.

In accordance with this discovery, it is an object of the invention to provide hybridomas which produce antibodies specific to protein components of the crystalline inclusion of *Bacillus thuringiensis* subsp. *israelensis*.

It is a further object of the invention to provide methods for preparing these hybridomas.

A still further object of the invention to provide antibodies which are monospecific for component proteins of the crystalline inclusion of *B. thuringiensis* subsp. *israelensis*.

A still further object of the invention is to provide immunochemical methods for use of the monoclonal antibodies for research and development of novel derivatives of the crystal proteins recognized by the antibodies, potentially constructed through, but not limited to, use of recombinant DNA technology.

A still further object of the invention is to provide immunochemical methods useful for monitoring development and construction of novel organisms containing the specific crystal proteins recognized by the monoclonal antibodies.

A still further object of the invention is to provide immunochemical means of monitoring the presence and/or quantitation of the protein or its derivatives recognized by the monoclonal antibodies including, but not limited to environmental monitoring, industrial production and quality control, or other qualitative or quantitative measurement of the proteins recognized by the monoclonal antibody.

DETAILED DESCRIPTION OF THE PREFERRED EMBODIMENTS

The mouse hybridoma cell line (Bti-1) which produces and secretes monoclonal antibody specific for crystal protein of *Bacillus thuringiensis* subsp. *israelensis* is on deposit at the American Type Culture Collection, 12301 Parklawn Drive, Rockville, Md. 20852. The hybridoma cell line deposit is designated as ATCC HB 9362. The date of deposit was Mar. 17, 1987.

The method of preparing the hybridomas and monoclonal antibodies of the preferred embodiment comprises the following:

Soluble crystal protein is mixed with an equal volume of Freund's complete adjuvant and injected intraperitoneally (i.p.) into 6–12 week old mice (BALB/c). This treatment is designed to stimulate (immunize) their immune systems to produce lymphoid cells which secrete antibodies (immunoglobulins) specific for antigenic sites (epitopes) of the component crystal proteins present in the immunizing material injected. The mice are allowed to rest for a period of time sufficient to allow their immune systems to respond to immunization and are then given 1–4 booster immunizations consisting of additional doses of soluble crystal protein of *B. thuringiensis* subsp. *israelensis* mixed with Freund's incomplete adjuvant. Spleens are aseptically removed from the immunized mice 3–4 days following the final booster immunization, and used to prepare suspensions of spleen cells (splenocytes) for use in subsequent cell fusion experiments.

Mouse myeloma cells that have continuous growth capability in cell culture medium are fused with the splenocytes from the immunized mice to form hybrid cells (hybridomas) that have characteristics of both of the parental cell types. Hybridomas are selected from the mixed cell population resulting from the fusion experiments based on their ability to grow in continuous culture in medium containing hypoxanthine, aminopterin, and thymidine (HAT medium). Myeloma cells useful for these preferred embodiments lack the enzyme hypoxanthine-guanine phosphoribosyl transferase, and are unable to survive in HAT selective medium. Exemplary myeloma cells for this invention are SP2/0-Ag14, which are derived from a hybrid produced from BALB/c splenocytes and X63-Ag8, a cell line frequently used to produce hybridomas.

In addition to their sensitivity to HAT medium, the myeloma cells are resistant to 20 ug/ml of 8-azaguanine and synthesize no immunoglobulin. Cells of the parental types which have not successfully fused to form hybridomas do not survive in HAT medium, whereas hybridoma cells grow and form colonies of cells all derived from the same hybrid parent cell. Immunoglobulins secreted by hybridoma colonies, if any, are determined by the characteristics of the splenocyte parental cell. Each hybridoma colony is derived from a single parental splenocyte and a myeloma cell. Therefore, since each splenocyte (lymphoblast, lymphocyte) parental cell secretes only one type of antibody, then each of the hybridoma colonies derived from the hybrid cells formed in the fusion experiments also secrete only one type of antibody.

Myeloma cells are maintained in suitable growth medium such as Dulbecco's Modified Eagle's Medium (DMEM) containing fetal bovine serum. Although DMEM was used, most other tissue culture media designed for growth of mammalian cells work equally well after a short adaptation period. Cells are subcultured to maintain a population density of about 100–500 thousand cells/ml.

Suitable techniques for cell fusion to obtain hybridomas are described infra in the more detailed example. Basically the spleen cells are fused with the myeloma cells in the presence of polyethylene glycol (PEG). Dimethylsulfoxide (DMSO) added to the PEG increases the yield of hybrid cells. Feeder cells such as mouse peritoneal macrophages or splenocytes from non-immunized mice are added to the cell suspension after fusion to aid in the establishment of hybridoma colonies by conditioning the growth medium. The cell suspension is diluted in DMEM HAT or with other appropriate medium and incubated under appropriate conditions to promote growth of hybrid cells. Small hybridoma colonies can be seen within about 5-7 days after the fusion. After 1 week, sufficient medium is added to allow continued growth of the colonies. At about 2 weeks after fusion, culture supernatant is tested for the presence of mouse antibody, or antibody specific for crystal protein of *B. thuringiensis* subsp. *israelensis*. Spent culture medium supernatant may be tested following additional growth of the hybridoma if desired. A number of different serologic and biochemical tests are known for evaluating the antibodies secreted by various hybridomas. In the preferred embodiments, a modified enzyme-linked immunosorbent assay (ELISA) was designed and developed and utilized for testing the hybridomas for production of antibody specific for crystal protein of *B. thuringiensis* subsp. *israelensis*. Essentially, the ELISA method consists of binding *B. thuringiensis* subsp. *israelensis* crystal protein antigen to polystyrene microtiter plates or pegs fitted to such plates. Nonfat dry milk is used to block available nonspecific binding sites on the polystyrene surface. Hybridomas are screened by addition of culture supernatant to antibody dilution buffer (ADB) and incubation with the polystyrene-bound antigen for sufficient time and at sufficient temperature to allow antibody to bind to the antigen. If a hybridoma secretes antibody which recognizes and binds to crystal protein of *B. thuringiensis* subsp. *israelensis*, the antibody forms a complex with the antigen bound to the polystyrene. The polystyrene surface with the bound antigen and antigen/antibody complexes are rinsed in ADB or water, followed by incubation with goat antimouse IgG (H+L) horseradish peroxidase conjugate diluted in ADB. If an antigen/antibody complex is bound to the polystyrene, then the goat antimouse IgG horseradish peroxidase conjugate (IgG-HRP) binds to the antibody member of the complex. Excess conjugate and milk are rinsed from the polystyrene with ADB or water; the polystyrene with bound complexes is then incubated in peroxidase substrate solution for sufficient time to allow color development. 2,2'-Azino-bis[3-ethyl]benzthiazolinesulfonic acid (ABTS) is a chromogen used to detect peroxidase activity. If the IgG HRP conjugate has bound to antibody/antigen complex on the polystyrene, peroxidase activity will cause the ABTS to form a green-colored product which can be quantitated spectrophotometrically. Antibody-secreting colonies routinely give absorbance values at least 5-fold higher than controls, and are selected for subcloning.

Subcloning of antibody-secreting colonies stabilizes the genetic composition of the cell line and antibody secretion by selecting against unstable, nonviable, and non-secreting derivatives. Subcloning is accomplished by subculturing limiting dilutions of cell suspensions in culture medium so that only single colonies develop. Alternately, subcloning is accomplished in semisolid growth medium containing agarose or other support matrix, and picking colonies to individual wells for growth and testing. Purified subclones secreting antibody can be propagated indefinitely, and routinely score up to 2000-fold higher absorbance values in the ELISA test compared to controls lacking antibody.

Antigen specificity of antibodies is determined by electrophoretic separation of *B. thuringiensis* subsp. *israelensis* crystal proteins and blotting onto a suitable support medium such as nitrocellulose membrane (Western blotting). The detailed procedures to accomplish this are described infra in the example given. Antibody is diluted in ADB or similar buffer, recognizing and binding only to its specific antigen. Antibody complexed to the bound antigen is resistant to being rinsed off the support matrix and is incubated with an antibody detection system such as goat anti-mouse IgG-HRP. After incubation with the goat anti-mouse IgG-HRP conjugate, the blot is rinsed and then incubated in a peroxidase substrate solution, containing a chromogen which forms an insoluble precipitate at the site of the peroxidase enzyme, thus marking the site of antibody bound to its specifically recognized antigen. If the antibody recognizes more than one protein, the sites on the blot corresponding to each of the recognized proteins will be marked by precipitated chromogen. Similarly, cross reaction with other proteins, including, but not limited to other crystal proteins are investigated by the immunoblotting technique. This procedure is used to establish the specificity of the monoclonal antibody for the crystal protein of *B. thuringiensis* subsp. *israelensis*. The antibody does not cross react with unrelated crystal proteins (including subsp. *kurstaki*) under the conditions specified. Therefore, the antibody discriminates between crystal proteins, binding only to that of subsp. *israelensis*, allowing the determination of *B. thuringiensis* subsp. *israelensis* crystal protein in complex mixtures even in the presence of crystal protein from other varieties of *B. thuringiensis*. Because of the specificity of the monoclonal antibody produced by the cloned hybridoma for specific crystal protein of *B. thuringiensis* subsp. *israelensis*, it is used to verify and quantitate the presence of said protein by immunoassay. This novel ability is important because of the need for standardized methods in quality control and quantitation of crystal protein in microbial pesticides based on *B. thuringiensis* subsp. *israelensis*.

The antibodies of the invention are also used in purification of the specific protein or related protein from complex mixtures through the use of affinity chromatography. Affinity chromatography techniques are general methods which work with antibodies of many different types and specificities. Essentially, the antibody is bound to a solid support matrix that can be brought into contact with the mixture containing the antigen recognized by the antibody, where it becomes bound by the antibody to the matrix. Alternately, the antibody is mixed with the antigen mixture and brought into close contact with a solid support matrix containing bound material which recognizes the antibody, binding both it and its bound antigen to the matrix. In either case, the mixture is rinsed away, leaving the antibody/antigen complex bound to the support matrix from which the complex can be disrupted by altering pH, salt, temperature, or other conditions to achieve elution from the matrix of one or more of the previously bound components. These techniques are used to purify the antigen and related proteins for use as a potential pesticide, a chemical reagent, or in combination with other substances.

The following example illustrates but is not intended to limit the scope of the invention.

EXAMPLE 1

Sources of Materials

Strains of *Bacillus thuringiensis* were obtained from the *B. thuringiensis* culture collection of the U.S. Dept. of Agriculture maintained at Brownsville, Tex. (H. Dulmage). BALB/c mice were purchased from Charles River Laboratories (Wilmington, Mass.) and maintained in a laboratory breeding colony. Murine myeloma SP2/0-AG14 was purchased from the American Type Culture Collection (ATCC CRL 1581, Rockville, Md.) and maintained in the laboratory tissue culture collection. Tissue culture medium, hybridoma-screened fetal calf serum, and supplements were obtained from Whittaker M.A. Bioproducts (Walkersville, Md.), or from Sigma Chemical Co. (St. Louis, Mo.). Dimethylsulfoxide (DMSO) and polyethylene glycol (PEG) were obtained from the American Type Culture Collection.

All cell cultures were in Dulbecco's Modified Eagle's Medium (DMEM) supplemented with 10% fetal calf serum, 2-4 mM L-glutamine, 4.5 g glucose per liter, 100 ug streptomycin and 100 U penicillin G per ml. Hypoxanthine (H), thymidine (T), and aminopterin (A) were included as indicated in the text at final concentrations of 100 uM, 16 uM, and 0.4 uM, respectively. All tissue cultures were incubated at 37° C. with 5-7% $CO_2$. Cell density and viability were determined in the presence of trypan blue using a hemocytometer.

Preparation of Antigen

*B. thuringiensis* subsp. *israelensis* (strain HD522) was grown in L-broth (10 g tryptone+5 g yeast extract+1 g glucose+5 g NaCl per liter), with aeration at 30° C. Synchronous sporulation was promoted by centrifuging the vegetative bacterial cells, resuspending in a phosphate-buffered glucose mineral salts medium, and continuing incubation until sporulation was complete. The sporulated culture was harvested by centrifugation, sonicated to break the spore-crystal complexes apart, and fractionated by density gradient centrifugation on renografin to purify the crystals (Temeyer, 1984). The procedures outlined therein hereby incorporated in this application by reference. Purified crystals were dialyzed in distilled water, freeze dried, suspended at 2-4 mg/ml in 50 mM $Na_2CO_3$ (pH 10.5) or in 50 mM NaOH, and incubated for 1-2 hr at 37°-45° C. to achieve solubilization of the component crystal proteins (Thomas and Ellar, 1983). The procedures outlined therein hereby incorporated by reference. 2-Mercaptoethanol (10 mM) was usually included to aid in solubilization of the crystals.

Immunization of Mice

Six to twelve-week-old BALB/c mice were immunized by i.p. injection of crystal protein antigen in adjuvant. Injections usually contained 50-100 ug crystal protein. One to four booster injections were made at two to four week intervals. Initial immunizations contained complete Freund's adjuvant and booster immunizations contained incomplete Freund's adjuvant. Immunized mice were bled prior to booster immunization and production of antibody specific for *B. thuringiensis* crystal protein was monitored by an enzyme-linked immunosorbent assay (ELISA).

Preparation of Myeloma Cells for Hybridization

Murine myeloma cells (SP2/0-AG14) were grown in DMEM. Cell densities of growing cultures were maintained between $1-5 \times 10^5$ cells/ml by subculturing. Each hybridization required approximately $10^8$ myeloma cells with better than 90% viability. On the day of hybridization, myeloma cells were collected by centrifugation and resuspended in DMEM lacking fetal bovine serum (serum-free DMEM).

Preparation of Splenocytes

Splenocytes were prepared from mouse spleens (removed aseptically) by grating through sterile stainless steel wire mesh screens into serum-free DMEM. Each spleen usually yielded approximately $10^8$ splenocytes. Splenocytes from non-immunized mice were used as feeder cells, or to condition growth medium. Splenocytes from immunized mice were hybridized with the myeloma cells.

Hybridization of Myeloma Cells and Splenocytes

Immune splenocytes were mixed with myeloma cells (in approximate 1:1 ratio) and pelleted by gentle centrifugation in serum-free DMEM. The supernatant was carefully removed and one ml PEG solution (45-50% PEG+5% DMSO in serum-free DMEM) was added and gently stirred with the cells for 1-2 min, being careful not to break apart small clumps of cells. The PEG was slowly diluted by slow addition, with stirring, of serum-free DMEM containing reduced amounts or lacking PEG. After dilution of PEG (to reduce viscosity), the cell suspension was gently centrifuged to pellet the cells, which were gently resuspended in DMEM (with fetal calf serum) plus HAT supplements. Splenocytes from a non-immunized mouse were added to the cell suspension and diluted with DMEM+HAT supplements to about $1-2 \times 10^6$ cells/ml and plated in 96 well tissue culture plates (0.1 ml/well). The plates were incubated at 37° C. with 7% $CO_2$ and greater than 90% relative humidity for one week after which 0.1 ml fresh DMEM (with serum) containing HT supplements was added. The plates were occasionally inspected for growth of hybridoma colonies. Hybridoma colonies were picked to individual wells if more than one colony was growing in the same well. Growth of colonies was supported by replacement of part of the spent medium with fresh HT-supplemented DMEM. Culture medium from wells containing hybridoma colonies was tested by ELISA for presence of antibody specific for *B. thuringiensis* subsp. *israelensis* crystal protein.

ELISA to Detect *B. thuringiensis* subsp. *israelensis* Crystal Protein-Specific Antibody Antigen was attached to polystyrene pegs or microtiter plates (not tissue culture treated) by incubation for 1 hr or longer at 37° C. of 0.2-2 μg soluble antigen per well in 10 mM potassium phosphate, pH 7.0, which was necessary to obtain uniform antigen binding. Buffer composition and concentration are critical to achieve uniformly high binding of soluble crystal protein. Other buffers which can also be used are: $NaCO_3$, $KPO_4$, Tris-HCl, Tris-acetate, Tris-citrate, Tris-$NaPO_4$, and Tris-glutamate. Some lots of polystyrene plates bind antigen poorly unless pretreated with glutaraldehyde. The Falcon Assay Screening Test ® (F.A.S.T. ® or FAST) system (Becton & Dickenson, Oxnard, Calif.) was used in preference to other tests, such as microtiter plates for antigen attachment for reasons of convenience; however, ordinary polystyrene microtiter plates work equally well although pretreatment with 0.1% glutaraldehyde for 1 hr may improve results for some manufacturer's lots of polystyrene plates. Nitrocellulose or nylon can also be substituted for polystyrene as a support medium for antigen attachment. Nonspecific binding sites on the polystyrene-antigen surface were blocked by incubation with 10% nonfat dry milk (Carnation) for at least one hour which was necessary to reduce nonspecific background.

Serum or tissue culture medium was tested for the presence of antibody specific for *B. thuringiensis* subsp. *israelensis* crystal protein by enzyme-linked immunosorbent assay (ELISA). The test serum or growth medium was diluted at least 1:4 (v/v) in antibody dilution buffer (ADB2) containing 2% (w/v) nonfat dry milk, 1% (v/v) Tween-80, and 0.01% (v/v) antifoam A (Sigma Chemical Co., St. Louis, Mo.) all in phosphate buffered saline or other physiological solution. Solutions containing alternate proteins, such as bovine serum albumin are also effective in reducing nonspecific binding of antibody. These factors were necessary to obtain uniform binding of available antibody in the absence of unacceptable background. ADB5 contained 5% (w/v) nonfat dry milk, but was otherwise equivalent to ADB2. The diluted serum or spent growth medium was incubated with the antigen (bound to polystyrene plates or pegs) with agitation. Incubation time and temperature are not critical. However, exemplary conditions would be between 15°-37° C. No loss of binding specificity was found with incubation times as long as 3-4 hours, even under condition of antibody excess. This is an unusual feature for an immunochemical assay obtainable as a result of the steps described supra. Most immunochemical assays are limited in achievable sensitivity due to non-specific background. In our example, the limiting factor on assay sensitivity was the availability of antibody, not non-specific binding of antibody. It was therefore possible to achieve even greater sensitivity by increasing the volume of antibody-containing solution tested by replacement of the test solution every hour or so. After incubation of the test solution to allow antibody to bind to the bound antigen, unbound or non-specifically bound antibody was removed by 1 min. or longer rinse in ADB2 or ADB5. ADB2 was used for dilution of test solutions potentially containing antibody, and ADB5 for rinses. The lower concentration of milk in ADB2 allowed more rapid binding of available antibody, while the higher concentration in ADB5 resulted in slightly better competition for non-specific binding sites and better removal of non-specifically bound antibody. Other buffers which can be used are: milk, milk and anti-foam A, milk and Tween-80, milk and Tween-80 and anti-foam A.

Where binding specificity is not critical, such as for assays during routine subcloning or simple verification of antibody activity, then water was used for rinse. Antibody which is specifically bound to the antigen was retained through the rinse and was monitored by use of immunoactive tracers which bind to mouse antibody. We used goat, anti-mouse-IgG (H+L) antibody conjugated to horseradish peroxidase (BioRad, Richmond, Calif. or Sigma Chemical, St. Louis, Mo.) to reveal the presence of mouse antibody. The peroxidase-conjugated antiserum was diluted in ADB2 (usually 1:250 or higher dilution) and incubated with the polystyrene-bound antigen, with agitation, to allow binding to mouse antibody which was specifically bound to the antigen. Use of ADB2 or similar buffer is important to prevent high background. Incubation conditions were similar to those described for test serum or growth medium. Excessively high concentration of antiserum-conjugate resulted in high background due to non-specific adsorbtion to polystyrene and bound proteins, and was eliminated by increasing the working dilution of the antibody-enzyme conjugate. We routinely used a dilution of 1:1000 with 1 hour incubation, but shortened the incubation time by using correspondingly lower dilutions if necessary. A rinse step as before was included to remove non-specifically bound antibody-enzyme conjugate. Presence of the horseradish peroxidase was revealed through oxidation of a chromagen such as 2,2'-azino-bis[3-ethyl]benzthiazolinesulfonic acid (ABTS) by incubation in 0.05M Na-citrate, pH 4.0, containing 2 mM $H_2O_2$ and 0.2 mM ABTS for up to 1 hour with agitation to allow color development. Microtiter plates were read on a Titertek Multiscan ® plate reader at 414 nm; other methods of determining absorbance values, although less convenient, work equally well. Wells containing antibody usually gave absorbance values 5-fold or more above control values obtained for negative control wells lacking antibody. Use of alternate enzyme substrates, or enzyme conjugates resulted in similar results. It was also possible to use enzyme- or radio-labeled Protein A, or a variety of other standard methods to reveal the presence of antibody.

Subcloning of Antibody-Secreting Hybridomas

Tissue culture wells identified by ELISA as containing *B. thuringiensis* crystal protein-specific antibody, were inspected for the presence of hybridoma colonies. Cells from wells containing one or more apparent hybridoma colonies were subcloned by limiting dilution or by dilution in semisolid growth medium to allow individual cells to develop into separate colonies of cells. Individual colonies were picked and grown in separate wells to allow testing for antibody production using the ELISA technique described above. Antibody-secreting subclones scored up to 2000-fold higher absorbance readings in the ELISA test than controls lacking antibody.

Cryopreservation of Hybridoma Cell Lines

Hybridoma cell lines which secreted monoclonal antibody were preserved by cryogenic storage in liquid nitrogen. Actively growing cells from cultures maintained at cell densities between $100-500 \times 10^3$ cells/ml were concentrated by centrifugation; suspended in DMEM+HT supplements containing 50% (v/v) fetal calf serum; and then dimethylsulfoxide (DMSO) was slowly added (by dropwise addition with stirring of an equal volume of DMEM+HT supplements containing 30% (v/v) DMSO). Final concentration of medium components was 25% fetal calf serum and 15% DMSO in DMEM+HT supplements. Final concentrations of serum between 10 and 90%, and of DMSO between 10 and 30% also worked. The cell suspension was slowly cooled in cryotubes to $-70°$ C. (at about 1° C. per min), and then transferred to liquid nitrogen for indefinite storage.

Production of Ascites Fluid

A representative sample (10) of BALB/c mice (8–10 week old males) were primed for ascites production by intraperitoneal (i.p.) injection of 0.5 ml pristane 14 days prior to i.p. injection of 100–200 thousand hybridoma cells. Ascites formation was visually monitored, and accumulated fluid was removed by i.p. tapping using a hypodermic syringe. Ascites fluid was tested for antibody specific for *B. thuringiensis* subsp. *israelensis* crystal protein by the ELISA test described supra. Concentration of specific antibody in ascites fluid was determined to be at least 250-fold higher than that of spent growth medium from tissue culture.

Characterization of Immunoglobulin Class and Subclass

Secreted antibody present in hybridoma culture supernatant was tested by a double immunodiffusion method in an agarose gel using a commercial mouse monoclonal antibody typing kit purchased from Miles Scientific, a division of Miles Laboratories, Inc., Naperville, Ill. 60566. The antibody was determined to be mouse IgG3.

Determination of Antibody Binding Specificity

Antibody binding specificity was determined by a Western blotting technique as follows: Proteins from *B. thuringiensis* subsp. *israelensis* or subsp. *kurstaki* spore/crystal complexes were solubilized for non-denaturing polyacrylamide gel electrophoresis as described by Thomas and Ellar (1983, the procedures outlined therein hereby incorporated in this application by reference), but with the addition of 2 mM phenylmethylsulfonyl fluoride (PMSF) to inhibit proteases; or for SDS polyacrylamide gel electrophoresis by boiling the spore/crystal complexes directly in SDS loading buffer (50 mM tris-HCl, pH 7.5, 1% [w/v] sodium dodecyl sulfate (SDS), 25 mM 2-mercaptoethanol, 2 mM PMSF, 1 mM ethylenediaminetetracetic acid (EDTA), 10% [w/v] glycerol, and 0.0025% [w/v] bromophenol blue). Proteins were electrophoretically separated on denaturing SDS polyacrylamide gels (SDS-PAGE) or on nondenaturing polyacrylamide gels (nondenaturing-PAGE) and transferred to nitrocellulose membranes by electroblotting. The nitrocellulose membranes were incubated for 1 hour in 10% (w/v) nonfat dry milk to block any available nonspecific binding sites on the nitrocellulose membrane, rinsed briefly to remove excess milk in 10 mM tris-HCl, pH 7.5, in phosphate-buffered saline, or in water, and dried for at least 1 hr at $60°-80°$ C. The dry blots were wetted in ADB5 and hybridoma culture supernatant was added to the ADB5 to give a final dilution of 1:50. The blot was incubated with agitation in the ADB5 containing monoclonal antibody for 1 hr at 22° C., then was rinsed three times for 1 min ea in ADB5. The rinsed membrane was agitated with ADB5 containing goat, anti-mouse-IgG (H+L) conjugated to horseradish peroxidase (diluted 1:2000 in ADB5) for 1 hr at 22° C., was again rinsed three times in ADB5, and was rinsed in 10 mM tris-HCl, pH 7.5, or other rinse suitable to remove excess milk. The blot was developed in 100 ml peroxidase substrate solution containing 10 mM tris-HCl, pH 7.5, 2.5 mg o-dianisidine, and 0.01% $H_2O_2$ for 20 min to develop a colored precipitate on protein bands to which the monoclonal antibody had bound. This procedure resulted in specific binding of the antibody to proteins derived from *B. thuringiensis* subsp. *israelensis* and detection of said proteins by formation of the colored precipitate due to peroxidase activity and oxidation of the o-dianisidine. Analysis of proteins from purified spores and crystals of *B. thuringiensis* subsp. *israelensis* and subsp. *kurstaki* revealed that the principle band made visible by this technique was a crystal protein component of approx. mol. wt. 68k from subsp. *israelensis*. It was noted that the antibody recognizes and binds to said protein on Western blots of proteins separated by either a non denaturing-PAGE or SDS-PAGE, demonstrating that the antibody recognizes an epitope which is not lost by denaturation of the protein. At low concentration of protein (0.04–15 ng) on the blots, or under conditions of decreased antibody concentration, this protein was the only band revealed by peroxidase.

Therefore, we have thus constructed and subcloned a specific murine hybridoma cell line which secretes IgG3 monoclonal mouse antibody which specifically recognizes and binds to the epitope of the 68k crystal protein of *Bacillus thuringiensis* subsp. *israelensis*; said hybridoma ATCC HB 9362 is on deposit at the American Type Culture Collection, Rockville, Md.

DISCUSSION

Experiments using polyclonal rabbit antiserum demonstrated the need for modification of the available ELISA procedures to increase the sensitivity and reduce nonspecific background of the assay to levels capable of detecting a few hybridoma cells secreting antibody to the crystal protein of *Bacillus thuringiensis* subsp. *israelensis*. In addition, the achievement of increased assay sensitivity demonstrated the need for reduced variability in binding of antigen to the support material. Comparison of the measured dilution titer with estimates of the number of antibody secreting cells in tissue cultures of our cloned hybidomas indicated that our ELISA method was able to detect less than 70 antibody-secreting cells per ml culture medium, or ca. 7 cells in a single well of a microtiter plate. We were able to construct, detect and successfully subclone antibody secreting hybridomas when no hybridoma colonies were discernible among the feeder cells. Additional increases in detection sensitivity were achieved with this method by using longer incubation times or larger samples of culture supernatant but the described method was sufficient for use in screening and selecting hybridomas.

We attempted to identify the antigenic specificity of our monoclonal antibody using Western blots of SDS polyacrylamide gels of solubilized spore/crystal complexes of B. thuringiensis subsp. israelensis and kurstaki. Nonspecific binding of our antibody to a large number of proteins was greatly reduced by (1) blocking the nitrocellulose with milk following electroblotting, and (2) incubation of the antibody in ADB5. Under optimal conditions, low-level cross reaction of the antibody with other proteins was apparent and concentration dependent. ADB5 or similar buffer was essential for reducing nonspecific binding of immunogloins to proteases and other protein-binding molecules.

Monoclonal antibodies to B. thuringiensis subsp. thuringiensis delta-endotoxin were constructed by Huber-Lukac et al. (1982). They reported that all of their monoclonal antibodies cross-reacted with protoxin in an ELISA test; however, their protoxin was simply crystal protein dissolved in 0.1N NaOH for 30 min at 37° C., a condition that probably generated a mixture of protoxin and derivatives, making their observation difficult to interpret. Resolutions of the protein structure, toxicity, and relatedness of different crystal proteins may require molecular cloning of the structural gene(s) for the proteins in question due to potential proteolytic action during crystal protein formation, crystallization or solubilization. The availability of monoclonal antibodies will aid investigations of the molecular biology of Bacillus thuringiensis subsp. israelensis by enabling both immunochemical studies of crystal proteins and molecular cloning of specific crystal protein genes.

We claim:

1. The hybridoma ATCC HB 9362 or a subclone thereof which produces and secretes monoclonal antibody that specifically binds to the 68K crystal protein of Bacillus thuringiensis subsp. israelensis.

2. Monoclonal antibody produced by the hybridoma of claim 1.

* * * * *